United States Patent

Maier

[11] 4,368,162
[45] Jan. 11, 1983

[54] PROCESS FOR PRODUCING AMINOMETHYLPHOSPHONIC ACID

[75] Inventor: Ludwig Maier, Arlesheim, Switzerland

[73] Assignee: Ciba-Geigy Corporation, Ardsley, N.Y.

[21] Appl. No.: 317,048

[22] Filed: Nov. 2, 1981

[51] Int. Cl.³ .............................................. C07C 9/38
[52] U.S. Cl. .............................. 260/502.5 G; 260/938; 260/944; 260/970; 260/502.5 D
[58] Field of Search ............................... 260/502.5, 970

[56] References Cited

U.S. PATENT DOCUMENTS 2,847,442  8/1958  Sallmann .......................... 260/502.5
4,053,505 10/1977  Dutra ............................... 260/502.5
4,235,809 11/1980  Redmore .......................... 260/502.5

OTHER PUBLICATIONS

Bull. Akad. Sci., (USSR), 1968, 585.
J. Amer. Chem. Soc. 75, 5278, (1953).
J. Chem. Soc. (c), 1349, (1966).
CA 45, 8444, (1951).
CA 46, 421, (1952).
CA 48, (1954).
J. Org. Chem. 29, 832, (1964).
Synth. Inorg. Metal Org. Chem. 2, 317.
Synthesis 1980, 906.

Primary Examiner—Joseph E. Evans
Attorney, Agent, or Firm—Karl F. Jorda

[57] ABSTRACT

Aminomethylphosphonic acid is produced by reaction of a hexahydro-1,3,5-triazine-N,N',N''-tris-carboxylic acid ester of the formula

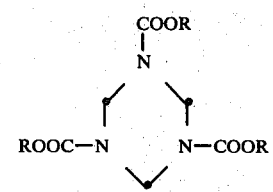

wherein R is an alkyl group having 1 to 4 carbon atoms or a phenyl group, in the presence of a Lewis acid as catalyst, with an ester of the phosphorous acid of the formula

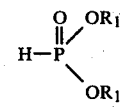

wherein $R_1$ is an alkyl group having 1 to 5 carbon atoms, a phenyl group, a benzyl group, the 2-cyanoethyl group or the 2,2,2-trichloroethyl group, to give an N-carboxyaminomethylphosphonic acid derivative of the formula

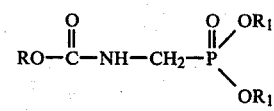

and subsequent hydrolysis thereof in an aqueous medium and in the presence of a strong acid.

Aminomethylphosphonic acid can be used as active substance for influencing plant growth, and as intermediate for producing herbicidal active substances.

13 Claims, No Drawings

PROCESS FOR PRODUCING AMINOMETHYLPHOSPHONIC ACID

The present invention relates to a process for producing aminomethylphosphonic acid of the formula

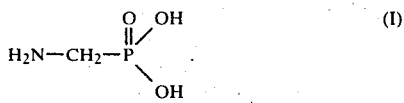

Aminomethylphosphonic acid has hitherto been described both as active substance for influencing plant growth (cp. German Offenlegungsschrift No. 2,315,886) and as intermediate for producing herbicidal active substances (cp. German Offenlegungsschrift No. 2,555,573).

It has already been suggested that aminomethylphosphonic acid can be produced by reaction of a carboxylic acid-N-hydroxymethylamide with phosphorus trichloride or with a trialkylphosphite and subsequent hydrolysis of the resulting reaction product (cp. U.S. Pat. Nos. 2,304,156 and 2,328,358 and Bull. Akad. Sci., (USSR) 1968, 585).

A further known process is based on the reaction of N-bromomethylphthalimide with sodium diethylphosphite or triethylphosphite and subsequent hydrolysis of the phthalimidomethylphosphonic acid diethyl ester (cp. Bull. Soc. Chim. (France), 778 (1948); Ann. Chim. (Paris) [12] 4, 372 (1954); J. Amer. Chem. Soc. 75, 5278 (1953); J. Chem. Soc. (c), 1349 (1966).

The process is also known of producing aminomethylphosphonic acid by reaction of O,O-diethyl-halomethylphosphonates with ammonia and subsequent hydrolysis of the reaction product obtained (cp. CA 45, 8444 (1951); ibid. 46, 421 (1952); ibid. 48, 564 (1954), or by reaction of chloromethylphosphonic acid with ammonia (cp. German Offenlegungsschrift No. 2,315,886).

A further suggestion which has been made is to produce aminomethylphosphonic acid by the Curtius decomposition of O,O-diethylphosphonoacetylhydrazide (cp. J. Org. Chem. 29, 832 (1964).

Also known is the method of producing aminomethylphosphonic acid by firstly reacting tert- butylamine with formaldehyde to give the corresponding Schiff base: (N-methylene-tert-butylamine), converting this by an addition reaction with a phosphorous acid diester into an N-tert-butylaminomethylphosphonate, and splitting off from this, with simultaneous hydrolysis of the ester groups, the tert-butyl group by reaction with hydrogen bromide under energetic conditions (cp. Synth. Inorg. Metal Org. Chem. 2, 317 (1972)).

Another known process for obtaining aminomethylphosphonic acid comprises the reaction of dibenzylamine with formaldehyde and a phosphorous acid ester to give an N,N-dibenzylaminomethylphosphonate, hydrolysis thereof, and subsequent detachment of the N-benzyl groups by hydrogenolysis. An alternative to this is a process wherein the N,N-dibenzylaminomethylphosphonic acid formed as intermediate in this synthesis is produced by reaction of dibenzylamine with chloroacetic acid to give N,N-dibenzylglycine, and further reaction thereof with phosphorus trichloride and phosphorous acid, the N-benzyl groups being then likewise split off from the resulting intermediate by hydrogenolysis (cp. Phosphorus and Sulfur 7, 333 (1979)).

According to a further known process, acetonitrile with formaldehyde (paraformaldehyde) is reacted with phosphorous acid and phosphorus trichloride, and the reaction product obtained is converted by further reaction with water into N-acetylaminomethylphosphonic acid, which yields, with the subsequent hydrolytic detachment of the acetyl group, aminomethylphosphonic acid (cp. German Offenlegungsschrift No. 2,829,046).

There is also known a method for producing aminomethylphosphonic acid, whereby benzylurethane is converted, by being heated with acetic anhydride and paraformaldehyde in acetic acid, into N-acetoxymethyl-benzylurethane; this is reacted with triphenylphosphite to give N-(O,O-diphenylphosphonomethyl)-benzylurethane, and from this the benzyloxycarbonyl group is split of by hydrolysis [cp. Synthesis 1980, 906].

It is not possible with the aforementioned processes to produce aminomethylphosphonic acid on a commercial scale with a satisfactory yield. With none of these processes is a total yield of more than 70% of theory attained. In most cases, the total yield is in the region of 20–50% of theory. Some of the processes mentioned in the foregoing are disadvantageous also in that expensive and difficultly obtainable starting materials are used. Furthermore, it is required in certain cases to apply extreme reaction conditions, which render a high expenditure on equipment necessary.

It is therefore the object of the present invention to provide a process which, starting with readily accessible starting materials, enables aminomethylphosphonic acid to be produced in a simple manner and in satisfactory yield.

It has been found that aminomethylphosphonic acid can be produced in a simple manner and in good yield by a process comprising reacting a hexahydro-1,3,5-triazine-N,N',N''-tris-carboxylic acid ester of the formula II

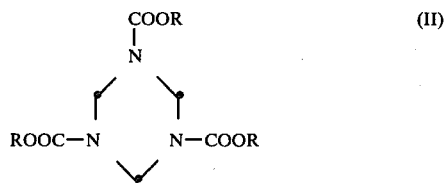

wherein R is an alkyl group having 1 to 4 carbon atoms or a phenyl group, at a temperature of 90°–150° C. and in the presence of a Lewis acid as catalyst, with an ester of the phosphorous acid of the formula III

wherein $R_1$ is an alkyl group having 1 to 5 carbon atoms, a phenyl group, a benzyl group, the 2-cyanoethyl group or the 2,2,2-trichloroethyl group, to give an N-carboxyaminomethylphosphonic acid derivative of the formula IV

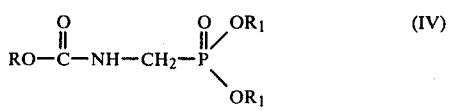

wherein R and $R_1$ have the meanings defined above, and subsequently hydrolysing this derivative in an aqueous medium, in the presence of a strong acid, to obtain aminomethylphosphonic acid.

The hexahydro-1,3,5-triazine-N,N',N"-tris-carboxylic acid esters of the formula II, which are required as starting material for the process according to the invention, can be produced in a simple manner and in excellent yield by reaction of corresponding urethanes with formaldehyde in an aqueous-hydrochloric acid medium (cp. J. Amer. Chem. Soc. 68, 1681 (1946)), or by reaction of the urethane with paraformaldehyde in the presence of p-toluenesulfonic acid as catalyst in toluene as solvent (cp. J. Heterocycl. Chem. 11, 937 (1974)). Among the hexahydro-1,3,5-triazine-N,N',N"-tris-carboxylic acid esters of the formula II thus obtained, the compounds particularly suitable as starting materials for the process according to the invention are those in which R is methyl or ethyl.

Suitable Lewis acids, which catalyse the reaction according to the invention of hexahydro-1,3,5-triazine-N,N',N"-tris-carboxylic acid esters of the formula II with esters of the phosphorous acid of the formula III, are in particular: boron trifluoride etherate, titanium tetrachloride, tin tetrachloride, iron(III)chloride and aluminium chloride. Boron trifluoride etherate has proved to be a particularly suitable catalyst. The Lewis acids are used as a rule in an amount of 1–10 mol %, relative to hexahydro-1,3,5-triazine-N,N',N"-tris-carboxylic acid ester of the formula II. The Lewis acids are preferably used in an amount of 4–6 mol %, relative to hexahydro-1,3,5-triazine-N,N',N"-tris-carboxylic acid ester of the formula II.

The reaction of a hexahydro-1,3,5-triazine-N,N',N"-tris-carboxylic acid ester of the formula II with an ester of the phosphorous acid of the formula III can be performed in either the presence or the absence of an inert solvent. Suitable solvents are for example hydrocarbons and halogenated hydrocarbons having a boiling point of at least 110° C., such as toluene, xylene, chlorobenzene and o-dichlorobenzene.

Within the given temperature range of 90°–150° C., in which the reaction according to the invention of hexahydro-1,3,5-triazine-N,N',N"-tris-carboxylic acid ester of the formula II with an ester of the phosphorous acid of the formula III can be performed, temperatures of 120°–150° C. are preferred.

Preferred esters of the phosphorous acid of the formula III are those wherein $R_1$ is an alkyl group having 1-3 carbon atoms. Likewise very suitable are the bis-(2-cyanoethyl) ester and the bis-(2,2,2-trichloroethyl) ester of phosphorous acid, since the 2-cyanoethyl group and the 2,2,2-trichloroethyl group can be split off by hydrolysis particularly readily.

The hexahydro-1,3,5-triazine-N,N',N"-tris-carboxylic acid esters of the formula II and the esters of the phosphorous acid of the formula III are as a rule reacted in a stoichiometric amount. Use of a slight excess of ester of the phosphorous acid of the formula III of up to 10 mol % has proved in practice to be advantageous.

For the hydrolysis of the N-carboxy-aminomethylphosphonic acid derivative of the formula IV, obtained by reaction of a hexahydro-1,3,5-triazine-N,N',N"-tris-carboxylic acid ester of the formula II with an ester of the phosphorous acid of the formula III, the aqueous reaction medium used can be either water or a mixture of water with an organic solvent, for example a mixture of water with acetonitrile, methanol or ethanol. Strong acids which can be used are for example: hydrochloric acid, hydrobromic acid, hydriodic acid, sulfuric acid, phosphoric acid and p-toluenesulfonic acid. Hydrohalic acids are especially suitable, particularly hydrochloric acid and hydrobromic acid. The hydrolysis of the N-carboxy-aminomethylphosphonic acid derivative of the formula IV is performed at elevated temperature, preferably at the reflux temperature of the reaction medium.

The radicals R and $R_1$ as alkyl groups can be straight-chain or branched-chain. A phenyl group R or $R_1$ can be unsubstituted, or substituted by substituents inert to the reactants, such as halogen, lower alkyl, alkoxy, cyano and nitro. The same applies for the phenyl group of the benzyl group $R_1$.

According to a preferred embodiment of the process according to the invention, aminomethylphosphonic acid is produced by reacting a hexahydro-1,3,5-triazine-N,N',N"-tris-carboxylic acid ester of the formula II wherein R is methyl or ethyl, in the presence of 4–6 mol % of boron trifluoride etherate, relative to the employed hexahydro-1,3,5-triazine-N,N',N"-tris-carboxylic acid ester of the formula II, at a temperature of 120°–150° C., with an ester of the phosphorous acid of the formula III, wherein $R_1$ is an alkyl group having 1 to 3 carbon atoms or a 2-cyanoethyl or 2,2,2-trichloroethyl group, to give an N-carboxy-aminomethylphosphonic acid derivative of the formula IV wherein R is methyl or ethyl, and $R_1$ is an alkyl group having 1 to 3 carbon atoms, 2-cyanoethyl or 2,2,2-trichloroethyl; and subsequently hydrolysing this derivative in an aqueous medium, in the presence of hydrochloric acid or hydrobromic acid, at the reflux temperature of the reaction medium, to thus obtain aminomethylphosphonic acid.

The process according to the invention for producing aminomethylphosphonic acid differs from the hitherto known processes in an advantageous manner in that both reaction steps, namely, both the reaction of a hexahydro-1,3,5-triazine-N,N',N"-tris-carboxylic acid ester of the formula II with an ester of the phosphorous acid of the formula III and the subsequent hydrolysis of the formed N-carboxy-aminomethylphosphonic acid derivative of the formula IV, result in a practically quantitative yield under reaction conditions which are easily maintained. Since moreover the hexahydro-1,3,5-triazine-N,N',N"-tris-carboxylic acid ester of the formula II, required as starting material, is obtainable in a simple manner in practically quantitative yield by reaction of corresponding urethanes with formaldehyde, the process according to the invention is suitable to a particular extent for the economical production of aminomethylphosphonic acid on a commercial scale.

The process according to the invention is further illustrated by the Examples which follow:

EXAMPLE 1

Production of O,O-diethyl-N-ethoxycarbonyl-aminomethylphosphonate.

2 ml of boron trifluoride etherate are introduced, with stirring, into a mixture of 20.22 g (0.066 mol) of hexahydro-1,3,5-triazine-N,N',N"-tris-carboxylic acid ethyl ester and 28.4 ml (0.22 mol) of diethyl phosphite at an internal temperature of 125° C. The temperature of the reaction mixture is then raised to 150° C. After 1 hour's stirring at 150° C., a further 2 ml of boron trifluoride etherate are added, in the course of which the temperature in the reaction mixture falls temporarily to 105° C. and subsequently slowly rises again to 150° C. The reaction mixture is afterwards again stirred for 1 hour at 150° C. The readily volatile constituents are then distilled off in high vacuum to obtain as residue 48.0 g (100% of theory) of O,O-diethyl-N-ethoxycarbonyl-aminomethylphosphonate. The product can be used without further purification directly for the following hydrolysis. It has a boiling point of 130° C./0.15 Torr.

EXAMPLE 2

Production of aminomethylphosphonic acid.

To 23.9 g (0.1 mol) of O,O-diethyl-N-ethoxycarbonylaminomethylphosphonate (crude product from Example 1) are added 100 ml of 20% hydrochloric acid, and the mixture is heated for 20 hours at reflux temperature. The hydrochloric acid is afterwards evaporated off in vacuo to obtain as residue 12.6 g of practically pure aminomethylphosphonic acid. Recrystallisation of the residue from water/acetone yields 9.4 g (84.7% of theory) of pure aminomethylphosphonic acid, m.p. 277°–281° C.

EXAMPLE 3

In the manner described in Example 1, the following products are obtained with the use of boron trifluoride etherate as the catalyst:

O,O-diethyl-N-methoxycarbonyl-aminomethylphosphonate, boiling point 130° C./0.08 Torr, by reaction of hexahydro-1,3,5-triazine-N,N',N''-tris-carboxylic acid methyl ester and diethyl phosphite;

O,O-dimethyl-N-methoxycarbonyl-aminomethylphosphonate, boiling point 125° C./0.08 Torr, by reaction of hexahydro-1,3,5-triazine-N,N',N''-triscarboxylic acid methyl ester with dimethyl phosphite; and O,O-dimethyl-N-ethoxycarbonyl-aminomethylphosphonate, boiling point 130° C./0.1 Torr, by reaction of hexahydro-1,3,5-triazine-N,N',N''-tris-carboxylic acid ethyl ester and dimethyl phosphite.

By hydrolysis of these products with aqueous hydrochloric acid or aqueous hydrobromic acid is obtained aminomethylphosphonic acid in a yield of 85–90% of theory.

What is claimed is:

1. A process for producing aminomethylphosphonic acid of the formula I

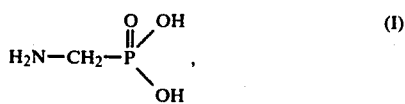

which process comprises reacting a hexahydro-1,3,5-triazine-N,N',N''-tris-carboxylic acid ester of the formula II

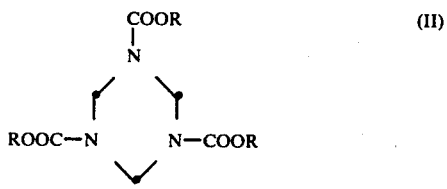

wherein R is an alkyl group having 1 to 4 carbon atoms, or a phenyl group, at a temperature of 90°–150° C. in the presence of a Lewis acid as catalyst, with an ester of the phosphorous acid of the formula III

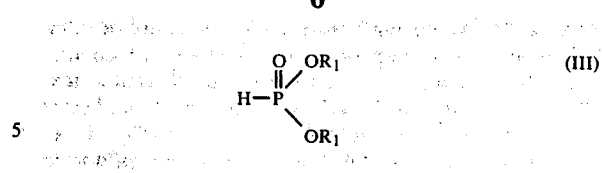

wherein $R_1$ is an alkyl group having 1 to 5 carbon atoms, a phenyl group, a benzyl group, the 2-cyanoethyl group or the 2,2,2-trichloroethyl group, to give an N-carboxyaminomethylphosphonic acid derivative of the formula IV

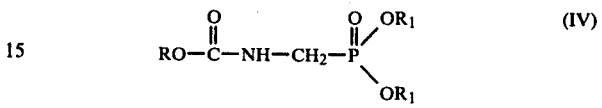

wherein R and $R_1$ have the meanings defined above, and subsequently hydrolysing this derivative in an aqueous medium, in the presence of a strong acid, to obtain aminomethylphosphonic acid.

2. A process according to claim 1, wherein the Lewis acid used is: boron trifluoride etherate, titanium tetrachloride, tin tetrachloride, iron(III)chloride or aluminium chloride.

3. A process according to claim 1, wherein the Lewis acid used is boron trifluoride etherate.

4. A process according to claim 1, wherein the Lewis acid is used in an amount of 1–10 mol %, relative to hexahydro-1,3,5-triazine-N,N',N''-tris-carboxylic acid ester of the formula II.

5. A process according to claim 1, wherein the Lewis acid is used in an amount of 4–6 mol %, relative to hexahydro-1,3,5-triazine-N,N',N''-tris-carboxylic acid ester of the formula II.

6. A process according to claim 1, wherein the reaction of a hexahydro-1,3,5-triazine-N,N',N''-tris-carboxylic acid ester of the formula II with an ester of the phosphorous acid of the formula III is performed at a temperature of 120°–150° C.

7. A process according to claim 1, wherein there is used as starting material a hexahydro-1,3,5-triazine-N,N',N''-tris-carboxylic acid ester of the formula II wherein R is methyl or ethyl.

8. A process according to claim 1, wherein there is used as starting material an ester of the phosphorous acid of the formula III wherein $R_1$ is an alkyl group having 1 to 3 carbon atoms, the 2-cyanoethyl group or 2,2,2-trichloroethyl group.

9. A process according to claim 1, wherein the ester of the phosphorous acid of the formula III is used in an excess of 3–10 mol %.

10. A process according to claim 1, wherein the strong acid used, in the presence of which the hydrolysis of an N-carboxy-aminomethylphosphonic acid derivative of the formula IV is performed, is: hydrochloric acid, hydrobromic acid, hydriodic acid, sulfuric acid, phosphoric acid or p-toluenesulfonic acid.

11. A process according to claim 1, wherein the strong acid used, in the presence of which the hydrolysis of an N-carboxy-aminomethylphosphonic acid derivative of the formula IV is performed, is a hydrohalic acid.

12. A process according to claim 1, wherein the hydrolysis of an N-carboxy-aminomethylphosphonic acid derivative of the formula IV is performed in water, or in a mixture of water with acetonitrile, methanol or ethanol, at the reflux temperature of the reaction medium.

13. A process according to claim 1, wherein a hexahydro-1,3,5-triazine-N,N',N''-tris-carboxylic acid ester of the formula II, wherein R is methyl or ethyl, is reacted in the presence of 4–6 mol % of boron trifluoride etherate, relative to the employed hexahydro-1,3,5-triazine-N,N',N''-tris-carboxylic acid ester of the formula II, at a temperature of 120°–150° C., with an ester of the phosphorous acid of the formula III, wherein $R_1$ is an alkyl group having 1 to 3 carbon atoms, a 2-cyanoethyl group or 2,2,2-trichloroethyl group, to give an N-carboxy-aminomethylphosphonic acid derivative of the formula IV, wherein R is methyl or ethyl, and $R_1$ is an alkyl group having 1 to 3 carbon atoms, 2-cyanoethyl or 2,2,2-trichloroethyl; and subsequently hydrolysing this derivative in an aqueous medium, in the presence of hydrochloric acid or hydrobromic acid, at the reflux temperature of the reaction medium, to obtain aminomethylphosphonic acid.

* * * * *